United States Patent [19]

Kling

[11] Patent Number: 5,582,668
[45] Date of Patent: Dec. 10, 1996

[54] METHOD AND ARRANGEMENT FOR MOUNTING ELASTIC ELEMENTS ONTO AN ELONGATED, MOVING MATERIAL WEB

[75] Inventor: Robert Kling, Skene, Sweden

[73] Assignee: Mölnlycke AB, Göteborg, Sweden

[21] Appl. No.: 392,805

[22] PCT Filed: Sep. 14, 1993

[86] PCT No.: PCT/SE93/00744

§ 371 Date: Mar. 15, 1995

§ 102(e) Date: Mar. 15, 1995

[87] PCT Pub. No.: WO94/06384

PCT Pub. Date: Mar. 31, 1994

[30] Foreign Application Priority Data

Sep. 15, 1992 [SE] Sweden .................................. 9202653

[51] Int. Cl.⁶ ........................................................ A61F 13/15
[52] U.S. Cl. .......................... 156/161; 156/160; 156/164; 156/177; 156/229; 156/433; 156/439; 156/441; 156/495; 156/496
[58] Field of Search ................................ 156/161, 164, 156/160, 229, 496, 495, 441, 177, 439, 433

[56] References Cited

U.S. PATENT DOCUMENTS 4,578,133  3/1986  Oshefsky et al. .................. 156/164
4,776,911  10/1988  Ude et al. ........................ 156/164 X
4,867,825  9/1989  Gidge ............................. 156/441 X

FOREIGN PATENT DOCUMENTS 464865     1/1992  European Pat. Off. .
WO90/00514 1/1990  WIPO .

*Primary Examiner*—Jeff H. Aftergut
*Attorney, Agent, or Firm*—Burns, Doane, Swecker & Mathis LLP

[57] ABSTRACT

A method and an arrangement for mounting elastic elements (T) on an elongated, moving material web (M), in which an elastic element extends between two holder elements (H) which are moved in a given direction and which elastic element extends essentially at right angles to the movement direction of the holder elements. According to the invention, different points on an elastic element which are mutually displaced transversely in relation to the movement direction are moved at mutually different speeds in relation to one another, and the elastic element is fastened to the material web subsequent to having achieved given distances in the movement direction between the different points on the elastic element, as a result of the different movement speeds.

10 Claims, 2 Drawing Sheets

METHOD AND ARRANGEMENT FOR MOUNTING ELASTIC ELEMENTS ONTO AN ELONGATED, MOVING MATERIAL WEB

BACKGROUND OF THE INVENTION

1. Field of the Invention

The present invention relates to a method and an arrangement for applying elastic elements to an elongated, moving web of material. The method and the arrangement are particularly intended for application when mounting leg elastic on diapers, incontinence guards and like absorbent articles.

2. Discussion of Related Art

When manufacturing such articles, they are often provided with elastic threads or bands in those parts which extend around the wearer's thighs when worn, so as to increase safety against leakage and to improve shape conformity to the wearer's thighs. In order for such leg elastic to extend around the thighs of the wearer of a modern pants-type diaper, it is necessary for the leg elastic to follow the outer contours of the diaper. One method of achieving this is known from Applicant's International Application WO 89/09550, according to which elastic threads are laid-out in curves, by guiding the threads in peripheral grooves of varying axial amplitude on a rotating roller. This method, however, can only be applied for mounting leg elastic essentially in the direction of movement of an underlying material web.

Applicant's International Patent Application WO 90/00514 discloses a method of mounting leg elastic transversely to the movement direction of an underlying material web, in which elastic threads are laid around thread holding elements by a rotating thread laying-out device, said elements moving at the same speed as an underlying material web, whereafter the threads are brought into contact with the web and fastened thereto. This method is primarily suitable for producing different patterns of elastic threads in which the threads extend linearly between the longitudinally extending edges of the material web. An intricate pattern of thread holding elements is required when wishing to mount the elastic threads in a curved shape, for instance so as to follow the outer contours of a diaper of hourglass shape.

OBJECTS AND SUMMARY

An object of the present invention is to provide a method and an arrangement by means of which elastic elements can be mounted on an elongated, moving web of material, such as to enable the elements to be mounted generally transverse to the movement direction of the web in a curved path which, for instance, coincides with the outer contour of a diaper of hourglass shape.

According to the present invention, this is achieved with a method of mounting elastic elements on an elongated, moving web of material in which an elastic element extends between two holder elements which can be moved in a given direction of movement, essentially at right angles to the movement direction of the holder elements, wherein the method is characterized in that different points of an elastic element are moved at different speeds in relation to one another transversely in relation to the direction of movement, and in that the elastic element is fastened to the material web subsequent to having achieved given distances in the movement direction between the different points of the elastic element as a result of the different movement speeds.

According to one preferred embodiment of the inventive method, the elastic element is gripped at least one point between the holder elements, this point being caused to move in the movement direction at a speed which differs from the speed at which the holder elements move.

According to one advantageous variant of the preferred embodiment of the inventive method, the holder elements are moved at the same speed as a moving material web onto which the elastic element located between the holder elements shall be mounted.

According to another advantageous variant of the preferred embodiment of the inventive method, the holder elements are moved at a speed which is different to the speed at which the material web onto which the elastic element that is located between the holder elements shall be mounted moves.

The invention also relates to an arrangement for mounting elastic elements onto an elongated, moving web of material, said arrangement including web moving means; means for moving at least a pair of mutually separated holder elements in a given direction; means for mounting an elastic element between the holder elements generally perpendicular to the movement direction; and means for fastening the elastic element to the web, wherein the arrangement is characterized by means for moving at least one point on the elastic element located between the holder elements at a speed different to the speed of points on the elastic element that are located in the neighbourhood of said at least one point.

BRIEF DESCRIPTION OF THE DRAWINGS

An exemplifying embodiment of the invention will now be described in more detail with reference to the accompanying drawings, in which.

DETAILED DESCRIPTION OF THE PREFERRED EMBODIMENTS

Figure 1:
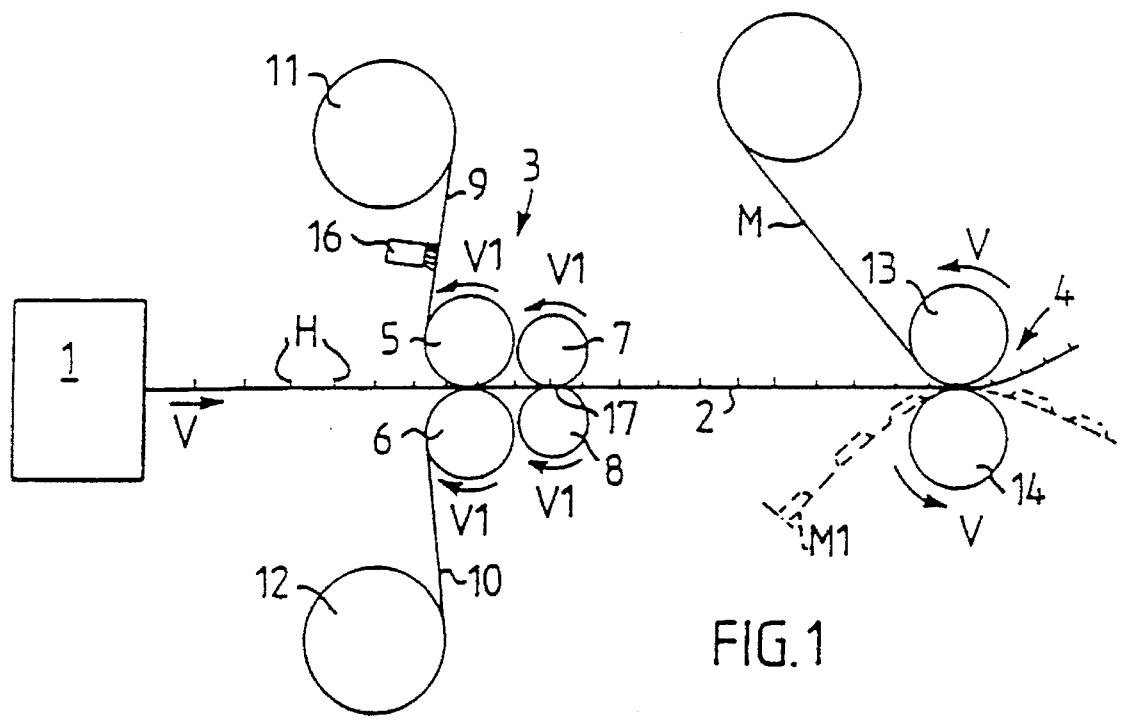
FIG. 1 illustrates schematically and in side view an embodiment of an inventive arrangement intended for mounting an elastic element on an elongated, moving web of material.

The arrangement illustrated in FIG. 1 comprises three main components, a thread laying-out device 1 which lays-out an elastic thread T in a square-wave pattern on holder elements H disposed on a moving conveyor means 2, a thread former 3 which imparts a V-shape to those parts of the elastic threads T which extend transversely to the direction of movement of the conveyor 2, with the apices of the V-shapes facing alternately in opposite directions, and a combining device 4 which combines the elastic threads T with a material web M and fastens the threads thereto. The laying-out device 1 may be any known device which is capable of laying-out elastic threads in a square-wave pattern, for instance a laying-out device of the type described in Applicant's aforesaid Patent Application WO 90/00514.

The thread former 3 includes a pair of rotationally driven rollers 5, 6 between which two webs 9, 10 of strip material can be fed from storage rollers 11, 12 to a web shearing device in the form of two rollers 7, 8, of which one roller 8 includes a knife 17, which at regular intervals cuts the webs 9, 10.

In the case of the illustrated embodiment, the combining device 4 is comprised of two rollers 13, 14 between which a material web M and the thread T held in a given pattern by means of the holder elements conveyor 2 pass, wherein the thread is fastened to the material web during its passage through the roll nip, for instance glued thereto. In the manufacture of diapers and similar absorbent articles, an additional material we M1 which supports absorption pads is conveniently passed through the rollers 13, 14, as indicated in broken lines in FIG. 1.

Figure 1A:
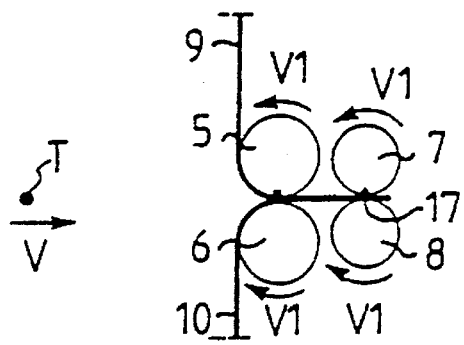
FIG. 1A is a cross-sectional view of a part of the arrangement shown in FIG. 1.

With reference primarily to FIGS. 2A–2D, which illustrate different stages of the movement of the holder element conveyor 2 through the thread former 3, the manner in which the thread former 3 illustrated in FIG. 1A operates will now be described.

Figure 2A:
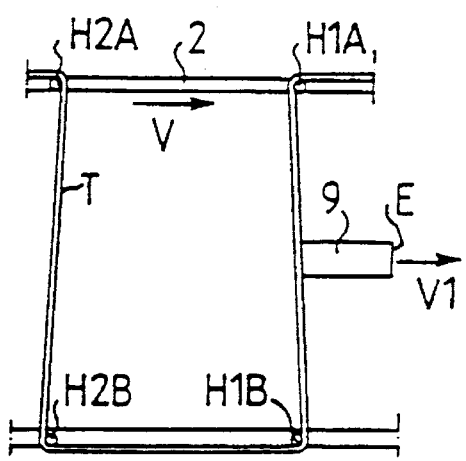
FIGS. 2A–2D illustrate schematically the manner in which a leg elastic is given an hourglass configuration in a first variant of the inventive method.

FIG. 2A is a part view of the holder elements H1A, H1B, H2A, H2B taken from above the arrangement illustrated in FIG. 1. The holder elements project upwardly from a conveyor 2, which is formed by two synchronously moving conveyors, and which holds an elastic thread T which has been placed by the laying-out device 1 around the holder elements H in a square-wave pattern. The conveyor 2 is advanced at a speed V, which is symbolized in FIGS. 1–2A with an arrow. In the FIG. 2A illustration, that part of the thread T which extends between the holder elements H1A and H1B has just arrived at the nip defined by the rotationally driven rollers 5, 6 of the thread former 3, which rollers have not been shown in this Figure for the sake of clarity, and are there located between the webs 9, 10 of strip material. These webs have been mutually combined during their earlier passage through the nip of the rollers 5, 6. These rollers are driven at a peripheral speed of V1, as indicated with arrows in FIGS. 1–2A. The speed V1 is lower than the speed V at which the holder element conveyor 2 moves. As a result of this speed difference, that part of the thread T which is located between the webs 9, 10 will move at a lower speed than the holder elements H1A and H1B.

Figure 2B:
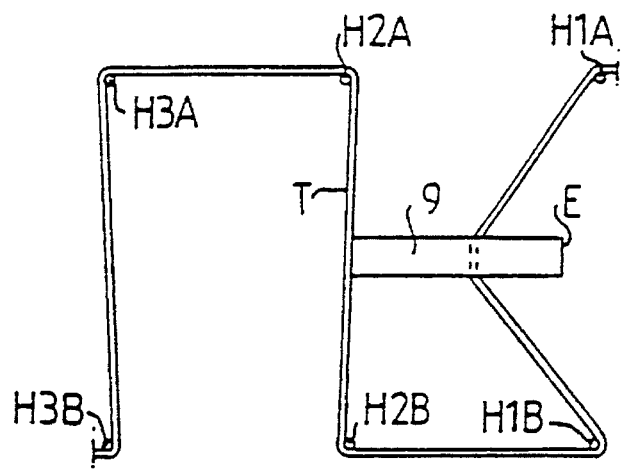

In FIG. 2B, that part of the thread T which is located between the holder elements H2A and H2B has reached the nip between the rollers 5, 6 of the thread former 3. The holder elements H1A and H1B have been moved a corresponding distance past the nip defined by the rollers 5, 6, whereas that part of the thread T held by and located between said holder elements has been moved a shorter distance, since the webs 9, 10, as before mentioned, move at a lower speed than the holder element conveyor 2. The part of the thread T which is located between the holder elements H1A and H1B has been given a V-shape, as a result of the difference in speeds between the holder elements and the webs 9, 10.

Figure 2C:
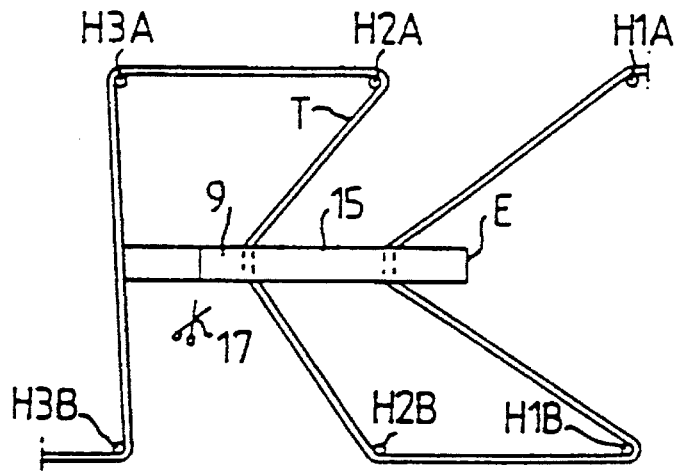
Figure 2D:
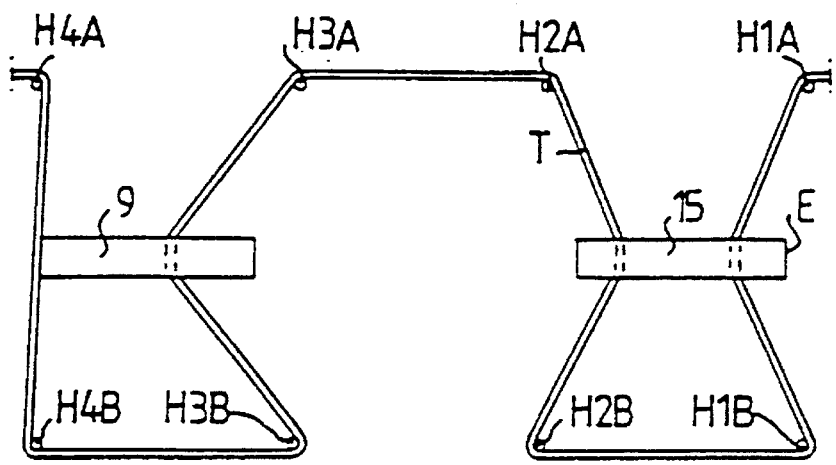

In FIG. 2C, that part of the thread T which is located between the holder elements H3A and H3B has reached the nip defined by the rollers 5, 6 of the thread former 3. The holder elements H2A and H2B have been moved through a corresponding distance and have taken those positions which the holder elements H1A and H1B earlier occupied at the stage illustrated in FIG. 2B, and that part of the thread T which is located between the holder elements H2A and H2B and held by the webs 9, 10 has taken the same position as that earlier occupied by the thread part located between the holder elements H1A and H1B in the stage of the thread forming process illustrated in FIG. 2B. The holder element H1A and H1B have also been moved through a distance corresponding to the distance moved by the other holder elements, whereas that part of the thread T located between these holder elements and held by the webs 9, 10 has been moved through a shorter distance. In this way, the thread T has been given a more acute V-shape between the holder elements H1A and H1B than between the holder elements H2A and H2B.

The rollers 7, 8 in the clipping device of the thread former 3 also rotate at the aforesaid peripheral speed V1 and therewith ensure that the combined webs 9, 10 are effectively guided. At the stage illustrated in FIG. 2A, the knife 17 has just severed the webs 9, 10 and the free end E of the combined webs 9, 10, shown in FIG. 2A, is located at the nip defined by the rollers 7, 8. At the stage illustrated in FIG. 2C, the roller 8 has rotated through one complete revolution and the knife 17 has returned to its position in the nip of the rollers 7, 8 and the webs 9, 10 have again been sheared. During the whole of the sequence of events illustrated in FIGS. 2A–2C, the webs 9, 10 have been influenced by the spring force inherent in the elastic thread T, which has been laid-out in a stretched state from the very beginning, i.e. in a stretched state relative to its tensionless length. The severed piece 15 of the webs 9, 10 is now free to move, and the spring force in the thread T strives to move the thread so that it will extend in a straight line between the holder elements and the severed piece 15 will therefore be moved by the thread T in the direction of movement of the conveyor 2 to the position of equilibrium between the holder elements H1A, H1B, H2A, H2B shown in FIG. 2D.

At the process stage illustrated in FIG. 2C, that part of the thread T which is located between the holder elements H3A and H3B has reached the position that was earlier occupied by the holder elements H1A and H1B at the process stage illustrated in FIG. 2A, and it will therefore clearly be seen that the described procedure relating to those parts of the thread T that are located between the holder elements H1A, H1B, H2A, H2B will be repeated cyclically for subsequent parts of the thread T. Thus, when the thread T is combined with the material web M in the combining device 4, the thread will have the form of a sequence of successive hourglass-shaped parts.

As before mentioned, the webs 9, 10 are mutually fastened together as they pass through the nip of the rollers 5, 6, which is best achieved by coating the web with glue with the aid of a glue applicator 16, as illustrated in FIG. 1. It is also conceivable to use other known fastener means. For instance, the webs 9, 10 can be welded together when made of a weldable material. It is also possible to use only one web of strip material, by fastening the thread directly to the web, although two webs are preferred in order to ensure that a stronger join is obtained. According to one variant, glue is applied intermittently, such that solely the regions adjacent the cuts made by the knife 17 will be joined together. In the case of such a variant, the thread T can be moved relative to the webs 9, 10 between the ends of the web piece 15 shown in FIGS. 2C and 2D, which means that the thread part located between the holder elements H2A and H2B will not be given the V-shape shown in FIG. 2C, since this part of the thread is able to move between the webs 9, 10 until it is stopped by the end-part E at which the webs 9, 10 are mutually, joined. However, the same end result is obtained as that obtained in FIG. 2D, since said thread part follows the opposite end-part of the web piece 15 when the end-part E is moved in the movement direction of the holder element conveyor 2 as a result of the spring force exerted by the thread part T located between the holder elements H1A and H1B.

As a comparison of FIG. 2A with 2D will show, the stretched or tensioned thread is stretched still further in this method. The tension in the thread, generated in the laying-out device 1, shall therefore be slightly less than is desired in the finished article. It will also be seen from FIGS. 2A–2D that the thread is stretched to a maximum during the process stage illustrated in FIG. 2C. If the tension in the thread of the finished article is so great as to create a risk that the thread will break when stretched to the aforesaid maximum, it is necessary to reduce the tension still further when laying-out the thread. In order to obtain the correct thread tension as the thread passes through the combining device 4, the distance between the holder elements transversely in relation to the movement direction is suitably increased. When the conveyor 2 is comprised of two conveyors, this distance can be readily obtained by causing the conveyors to diverge mutually after exiting from the thread former. It is also conceivable to use journalled holder elements having a minimum of friction, so as to enable a greater part of the length extension of the thread during the method to be effected by drawing more thread from the thread reel which delivers thread to the thread laying-out device. Another possibility is to journal the holder elements for movement in a transverse direction relative to the direction of movement of the conveyor means 2, for example by resiliently mounting the holder elements for movement in transverse grooves in the conveyor.

It will be understood that the described thread former 3 can be modified in many ways within the scope of the invention. For instance, the clipping or shearing device may be comprised of so-called flying shears or the like and the webs 9, 10 may be displaced horizontally in relation to the positions illustrated in FIGS. 2A–2D, i.e. upwardly or downwardly in said Figures. Neither need the holder element conveyor 2 move horizontally. It is also possible to hold stationary that part of the thread which extends between the holder elements H1A and H1B with the aid of some suitable device, until the thread part located between the holder elements H2A and H2B has been moved in a rectilinear state to the proximity of the first-mentioned thread part, and to then wrap said thread parts with a strip-like element and there-elements H1A and H1B. As will be understood, the thread former will have a totally different construction than the illustrated thread former when applying the inventive method in this way.

Figure 3:
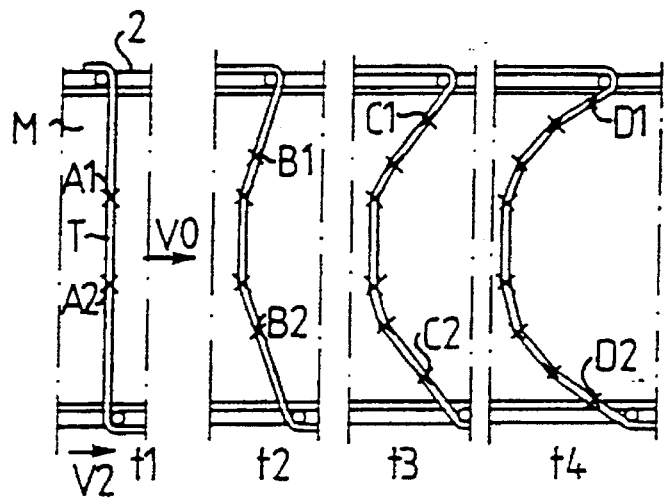
FIG. 3 illustrates schematically a second variant of the inventive method.

The variant of the inventive method illustrated in FIG. 3 differs from the aforedescribed variant primarily because the elastic thread T is fastened successively directly to the material web in a punctiform fashion, instead of being fastened to the web after the thread has been completely shaped., as is the case in the earlier described variant.

FIG. 3 illustrates the thread-forming procedure with the aid of instantaneous views which correspond to respective time points t1–t4.

The holder element conveyor 2 is combined with the material web M at time point t1 so that those parts of the thread T which extends transversely to the movement direction will be located immediately above the material web M, said thread T being laid-out on the conveyor 2 in a square pattern in the same manner as that in the earlier described embodiments of the inventive method. At the same time, the thread T is fastened to the material web at the points A1, A2 with the aid of suitable means. The material web M moves at a speed V0, whereas the holder element conveyor 2 moves at a speed V2 which is greater than V0. At time point t2, that part of the thread which is located between the points A1, A2 and is fastened to the slower moving material web will have moved through a shorter distance than the holder elements between which the thread part extends, and the thread parts which are located between respective fastening points A1, A2 and nearest holder element will extend obliquely in relation to said transverse direction. At B1, B2, the obliquely extending thread parts will be fastened to the material web at the time point t2, whereafter the thread part located between the points B1 and B2 will move at the speed V0. Those parts of the thread which lie outside the fastening points B1, B2 will then be given a progressively greater inclination or slope in relation to the transverse direction until they are fastened to the material web at the points C1, C2 at time point t3. Analogously herewith, those parts of the thread which are located outside the points C1, C2 will be given a greater angle of inclination in relation to the transverse direction than those parts of the threads which extend between the fastening points B1–C1 and B2–C2 respectively. At the time point t4, the thread is fastened finally to the opposing longitudinal edges of the material web M at points D1, D2.

When applying the variant of the inventive method illustrated in FIG. 3, the speed V2 of the holder element conveyor 2 is greater than the speed V0 of the material web M. It will be seen that if, instead, the holder element conveyor 2 is moved at a lower speed than the material web, so that the absolute speed difference will be equally as great but, in other respects, the same devices as those illustrated in FIG. 3 are used to fasten the thread T to the material web in a punctiform fashion, then the thread will be fastened to the material web in a mirror image relationship to the thread shown in FIG. 3. When the method described with reference to FIG. 3 is to be used to impart an hourglass configuration to the thread fastened to the material web, the thread is laid-out in a square pattern alternately on two holder element conveyors, of which one moves at a higher speed than the material web and the other moves at an equally lower speed. The thread is fastened to the material web in any suitable desired manner, for instance is glued to the web by first applying glue points thereto, and then pressing the thread onto the glue points, or by applying fastener tape to the thread and to the material web at the thread fastening points.

In the case of the method illustrated in FIG. 3, the tension in the thread will increase subsequently in those parts of the thread which lie outside the fastening points. If a uniform thread tension is desired, the rows of holder elements located on both sides of the material web and carried by belts, for instance, may be caused to converge towards each other, so as to compensate for the increase in the length of the thread part which is located between two mutually opposing holder elements as a result of curving this part from its transverse state.

It will be understood that the method illustrated in FIG. 3 can be modified in a number of ways without departing from the scope of the invention. For instance, other curve forms than those described can be obtained by changing the positioning and the number of the fastening points. Furthermore, S-shaped curves, for instance, can be obtained when the speed at which the holder element conveyors move can be varied. Those parts of the thread which extend transversely between the mutually opposing holder elements need not form parts of a square wave-laid thread, but may consist of separate elements fastened in the holder elements. The thread may also extend obliquely in relation to the transverse direction from the very beginning, when this is favourable to shaping the thread to a desired curve form. Neither need the elastic element consist of a single thread, but may consist of several threads, bands or the like.

I claim:

1. A method for mounting elastic elements on an elongated, moving material web, comprising the steps of:

extending an elastic element between two holder elements which are moved in a given direction at a first speed, and in which a portion of said elastic element extends generally at right angles to the movement direction of the holder elements;

mutually displacing different points of the portion of the elastic element with respect to each other in relation to the movement direction by moving one of said different points at a different speed than said first speed; and fastening the elastic element to the material web subsequent to achieving a given distance between the different points of the elastic element in the movement direction as a result of the different movement speeds.

2. The method according to claim 1, wherein the elastic element is gripped at at least one point between the holder elements, said point being caused to move in the movement direction at a speed which is different from the first speed at which the holder elements move.

3. The method according to claim 2, wherein the holder elements are moved at the same speed as the moving material web on which the elastic element located between the holder elements is to be mounted.

4. The method according to claim 2, wherein the holder elements are moved at a different speed than the moving material web on which the elastic element located between the holder elements is to be mounted.

5. The method according to claim 4, in which the elastic element is moved immediately above the material wherein, the elastic element is fastened to the material web at at least one point which is located between longitudinal edges of the material web so as to be given a speed (V0) which is different than the speed of those parts of the elastic element which from the fastening point concerned extend free from other fastening points to one of the longitudinal edges of the material web.

6. An arrangement for mounting at least one elastic element on an elongated, moving material web, comprising:

material web moving means, means for moving at least a pair of mutually separated holder elements in a movement direction, means for applying an elastic element located between the holder elements generally at right angles to the movement direction, means for fastening the elastic element to the material web, and means for moving at least one point on the elastic element located between the holder elements at a speed which is different than a speed at which points on the elastic element adjacent to said holder elements move.

7. The arrangement according to claim 6, in which an elastic element is laid-out in a square-wave pattern on holder elements carried by a holder element conveyor, wherein the means for moving at least one point on those parts of the elastic element located between the holder elements and extending transversely in relation to the movement direction at a speed which is different than the speed at which points on the elastic element adjacent to said holder elements move includes two rotatable rollers which define therebetween a nip through which a part of the transverse parts of the elastic element and at least one strip material pass; drive means for the rollers which are intended to drive said rollers at a peripheral speed which is lower than the speed of points on the elastic element adjacent to the holder elements; means for joining the strip material to the elastic element; and cutting means for cutting the strip material into pieces onto which two mutually sequential, transverse parts of the square-wave pattern of the elastic element are fastened.

8. The arrangement according to claim 6, wherein the means for moving at least one point on the elastic element located between the holder elements at a speed which is different than the speed at which points of the elastic element adjacent thereto includes means which function to move the holder elements at a speed (V2) which differs from the movement speed (V0) of the material web, so that the elastic element located between the holder elements will be stretched transversely across the material web and immediately thereabove, and means for fastening different points of the elastic element to the material web at given time intervals.

9. The arrangement according to claim 8, in which a sequence of holder element pairs carrying elastic elements transversely in relation to the movement direction is moved above the material web, wherein each alternate holder element pair is disposed on a holder element conveyor which is driven at a higher speed than the material web, and in that each other alternate holder element pair is disposed on a holder element conveyor which is driven at a slower speed than the material web.

10. The arrangement according to claim 8, further including by drive means for moving the holder element pairs at a variable speed.

* * * * *

UNITED STATES PATENT AND TRADEMARK OFFICE
CERTIFICATE OF CORRECTION

PATENT NO.   : 5,582,668
DATED        : December 10, 1996
INVENTOR(S)  : Robert KLING It is certified that error appears in the above-indentified patent and that said Letters Patent is hereby corrected as shown below:

In Column 5, line 38, after "there-" insert -- after release the thread part located between the holder --.

Signed and Sealed this

Twenty-second Day of April, 1997

Attest:

BRUCE LEHMAN

*Commissioner of Patents and Trademarks*

*Attesting Officer*